US009492673B2

(12) United States Patent
Carcieri et al.

(10) Patent No.: US 9,492,673 B2
(45) Date of Patent: Nov. 15, 2016

(54) PARAMETER VISUALIZATION, SELECTION, AND ANNOTATION INTERFACE

(71) Applicant: Boston Scientific Neuromodulation Corporation, Valencia, CA (US)

(72) Inventors: Stephen Carcieri, Los Angeles, CA (US); Dean Chen, Irvine, CA (US); Micahel A. Moffitt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/987,587

(22) Filed: Jan. 4, 2016

(65) Prior Publication Data
US 2016/0114179 A1 Apr. 28, 2016

Related U.S. Application Data

(62) Division of application No. 14/011,836, filed on Aug. 28, 2013, now Pat. No. 9,227,074.

(60) Provisional application No. 61/753,232, filed on Jan. 16, 2013, provisional application No. 61/699,115, filed on Sep. 10, 2012, provisional application No. 61/699,135, filed on Sep. 10, 2012, provisional application No. 61/693,866, filed on Aug. 28, 2012.

(51) Int. Cl.
*A61N 1/00* (2006.01)
*A61N 1/372* (2006.01)
*A61N 1/36* (2006.01)
*A61N 1/05* (2006.01)
*G06F 19/00* (2011.01)

(52) U.S. Cl.
CPC ......... *A61N 1/37247* (2013.01); *A61N 1/0534* (2013.01); *A61N 1/3605* (2013.01); *A61N 1/36185* (2013.01); *A61N 1/372* (2013.01);
(Continued)

(58) Field of Classification Search
CPC ............ A61N 1/0534; A61N 1/3605; A61N 1/36082; A61N 1/372; A61N 1/37241; A61N 1/36185; A61N 1/37235; A61N 1/37247; G06F 19/3406
See application file for complete search history.

(56) References Cited

U.S. PATENT DOCUMENTS

2008/0154340 A1 6/2008 Goetz et al.
2009/0287271 A1 11/2009 Blum et al.
(Continued)

FOREIGN PATENT DOCUMENTS

WO 2007/097861 A1 8/2007
WO 2009/097224 A1 8/2009

OTHER PUBLICATIONS

International Search Report and Written Opinion for PCT/US2014/027782 mailed Jun. 25, 2014.
(Continued)

*Primary Examiner* — Mallika D Fairchild
(74) *Attorney, Agent, or Firm* — Lowe Graham Jones PLLC; Bruce E. Black (57) ABSTRACT

A system and method for providing a user interface by which to display and/or control stimulation parameter settings includes a processor displaying a ray at an angle from a predetermined direction, and about a point representing a leadwire, that corresponds to a direction at which an electrical field is produced by respective electrical settings of one or more directional electrodes of the leadwire, and whose ray length corresponds to an electrical amplitude of an electrical parameter of the one or more directional electrodes.

20 Claims, 5 Drawing Sheets

(52) U.S. Cl.
CPC ....... *G06F 19/3406* (2013.01); *A61N 1/36082* (2013.01)

(56) References Cited

U.S. PATENT DOCUMENTS

2009/0287272 A1 11/2009 Kokones et al.
2009/0287273 A1 11/2009 Carlton et al.
2009/0287467 A1 11/2009 Sparks et al.
2010/0049276 A1 2/2010 Blum et al.
2011/0172737 A1 7/2011 Davis et al.
2011/0307032 A1 12/2011 Goetz et al.
2012/0302912 A1 11/2012 Moffitt et al.

OTHER PUBLICATIONS

Official Communication for U.S. Appl. No. 14/011,836 mailed May 20, 2015.

PARAMETER VISUALIZATION, SELECTION, AND ANNOTATION INTERFACE

CROSS-REFERENCE TO RELATED APPLICATIONS

The present application is a divisional of U.S. patent application Ser. No. 14/011,836 filed Aug. 28, 2013, which issued as U.S. Pat. No. 9,227,074, which claims priority to U.S. Provisional Patent Application Ser. No. 61/693,866 filed on Aug. 28, 2012, 61/699,135 filed on Sep. 10, 2012, 61/699,115 filed on Sep. 10, 2012, and 61/753,232 filed on Jan. 16, 2013, the content of all of which is hereby incorporated by reference herein in their entireties.

FIELD OF THE INVENTION

The present invention relates to a system and method for providing a user interface in which a representation of stimulation parameters of an electrode leadwire is provided, and via which to set and annotate such parameters.

BACKGROUND

Stimulation of anatomical regions of a patient is a clinical technique for the treatment of disorders. Such stimulation can include deep brain stimulation (DBS), spinal cord stimulation (SCS), Occipital NS therapy, Trigemenal NS therapy, peripheral field stimulation therapy, sacral root stimulation therapy, or other such therapies. For example, DBS may include stimulation of the thalamus or basal ganglia and may be used to treat disorders such as essential tremor, Parkinson's disease (PD), and other physiological disorders. DBS may also be useful for traumatic brain injury and stroke. Pilot studies have also begun to examine the utility of DBS for treating dystonia, epilepsy, and obsessive-compulsive disorder.

However, understanding of the therapeutic mechanisms of action remains elusive. The stimulation parameters, electrode geometries, or electrode locations that are best suited for existing or future uses of DBS also are unclear.

For conducting a therapeutic stimulation, a neurosurgeon can select a target region within the patient anatomy, e.g., within the brain for DBS, an entry point, e.g., on the patient's skull, and a desired trajectory between the entry point and the target region. The entry point and trajectory are typically carefully selected to avoid intersecting or otherwise damaging certain nearby critical structures or vasculature. A stimulation electrode leadwire used to provide the stimulation to the relevant anatomical region is inserted along the trajectory from the entry point toward the target region. The stimulation electrode leadwire typically includes multiple closely-spaced electrically independent stimulation electrode contacts.

The target anatomical region can include tissue that exhibit high electrical conductivity. For a given stimulation parameter setting, a respective subset of the fibers are responsively activated. A stimulation parameter can include a current amplitude or voltage amplitude, which may be the same for all of the electrodes of the leadwire, or which may vary between different electrodes of the leadwire. The applied amplitude setting results in a corresponding current in the surrounding fibers, and therefore a corresponding voltage distribution in the surrounding tissue. The complexity of the inhomogeneous and anisotropic fibers makes it difficult to predict the particular volume of tissue influenced by the applied stimulation.

A treating physician typically would like to tailor the stimulation parameters (such as which one or more of the stimulating electrode contacts to use, the stimulation pulse amplitude, e.g., current or voltage depending on the stimulator being used, the stimulation pulse width, and/or the stimulation frequency) for a particular patient to improve the effectiveness of the therapy. Parameter selections for the stimulation can be achieved via tedious and variable trial-and-error, without visual aids of the electrode location in the tissue medium or computational models of the volume of tissue influenced by the stimulation. Such a method of parameter selection is difficult and time-consuming and, therefore, expensive. Moreover, it may not necessarily result in the best possible therapy.

Systems have been proposed that provide an interface that facilitates parameter selections. See, for example, U.S. patent application Ser. No. 12/454,330, filed May 15, 2009 ("the '330 application"), U.S. patent application Ser. No. 12/454,312, filed May 15, 2009 ("the '312 application"), U.S. patent application Ser. No. 12/454,340, filed May 15, 2009 ("the '340 application"), U.S. patent application Ser. No. 12/454,343, filed May 15, 2009 ("the '343 application"), and U.S. patent application Ser. No. 12/454,314, filed May 15, 2009 ("the '314 application"), the content of each of which is hereby incorporated herein by reference in its entirety.

Such systems display a graphical representation of an area within which it is estimated that there is tissue activation or volume of activation (VOA) that results from input stimulation parameters. The VOA can be displayed relative to an image or model of a portion of the patient's anatomy. Generation of the VOA is based on a model of fibers, e.g., axons, and a voltage distribution about the leadwire and on detailed processing thereof. Performing such processing to provide a VOA preview in real-time response to a clinician's input of parameters is not practical because of the significant required processing time. Therefore, conventional systems pre-process various stimulation parameter settings to determine which axons are activated by the respective settings.

Those systems also provide interfaces via which to input selections of the stimulation parameters and notes concerning therapeutic and/or side effects of stimulations associated with graphically represented VOAs.

The leadwire can include cylindrically symmetrical electrodes, which, when operational, produce approximately the same electric values in all positions at a same distance from the electrode in any plain that cuts through the electrode. Alternatively, the leadwire can include directional electrodes that produce different electrical values depending on the direction from the electrode. For example, the leadwire can include multiple separately controllable electrodes arranged cylindrically about the leadwire at each of a plurality of levels of the leadwire.

SUMMARY

The electrical variation about a leadwire produced by directional electrodes of a leadwire creates an added layer of complexity concerning stimulation parameters and their effects. Example embodiments of the present invention provide an interface that includes a representation of a stimulation parameter for directional electrodes, via which to input settings therefor, and/or via which to obtain and/or output annotations concerning stimulation parameters thereof.

BRIEF DESCRIPTION OF THE DRAWINGS

In the drawings, which are not necessarily drawn to scale, like numerals may describe similar components in different views. The drawings illustrate generally, by way of example, but not by way of limitation, various embodiments discussed in the present document.

DETAILED DESCRIPTION

Figure 1:
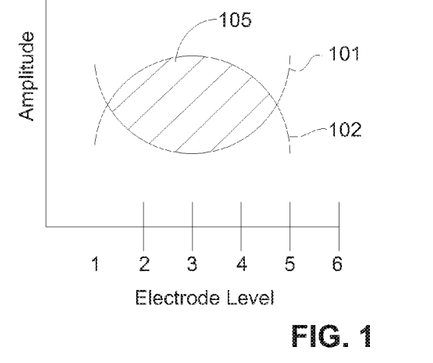
FIG. 1 shows graphs providing stimulation amplitude information for cylindrically symmetrical electrodes, according to an example embodiment of the present invention.

FIG. 1 shows an example graphical user interface display of output indicating amplitude information for stimulation using a cylindrically symmetric leadwire. With respect to a cylindrically symmetric leadwire, in an example embodiment, a graph is output in which stimulation amplitude values are plotted, for both a therapy onset curve 101 and side effect onset curve 102, against electrode location, where the electrode locations refer to longitudinal positions of the leadwire. For example, discrete positions along the abscissa can correspond to respective electrodes of the leadwire in their order of arrangement along the leadwire.

Alternatively, different combinations of amplitudes of the electrodes can be set, where each combination can be characterized as having an amplitude setting at a respective longitudinal position of the leadwire, producing a cylindrically symmetric stimulation about the leadwire at that respective longitudinal leadwire position. Positions along the abscissa can represent discrete locations from a first position of the leadwire towards another position of the leadwire, where some of the locations can be those of respective ones of the cylindrically symmetrical electrodes, and others can be other locations corresponding to the combination of stimulation settings of a plurality of the electrodes.

The therapy onset curve 101 indicates amplitude thresholds at which a therapeutic result is expected, depending on the electrode or longitudinal leadwire position at which the respective stimulation amplitude is set. The side effect onset curve 102 indicates a maximum stimulation amplitude at respective electrode or longitudinal leadwire positions, above which the stimulation is expected to cause an adverse side effect. Information on which the curves 101 and 102 are based can include empirically obtained data and/or model-based data. The graphs 101 and 102 can be specific to an indicated desired therapy and/or to an indicated adverse side effect. For example, the graphical user interface, e.g., in a target settings section, can include an input field for inputting a desired therapeutic effect and/or side effect to be avoided, and output a graph such that shown in FIG. 1 as information on which the user, e.g., a clinician, can determine settings to set in the system for producing a stimulation.

Such graphs can be useful for a clinician to eyeball a target range of possible target settings for one or more of the electrodes. For example, the clinician likely would choose to try an amplitude settings that falls at about the center of the shaded area 105 between the curves 101 and 102 since it is that region that is expected to produce a therapeutic effect and to avoid production of an adverse side effect.

However, such a representation does not reflect variations in amplitude at different directions cylindrically about the leadwire using directional electrodes. According to an example embodiment of the present invention, the system and method outputs stimulation amplitude information in a coordinate system in which each plotted data point is identified by a longitudinal position 'z', angle of rotation 'θ', and radius from center 'r', where the longitudinal position is the longitudinal position along the central axis of the leadwire, e.g., a distance from one of the ends, the angle of rotation is an angle between a selected direction extending outward from the leadwire, perpendicularly to the central axis thereof, and the direction in which stimulation is characterized as being produced by an electrode (or combination of electrodes), and radius is a distance from the leadwire along the direction in which the stimulation is characterized as being produced. The radius coordinate corresponds to the stimulation amplitude value, whereas the longitudinal position and angle of rotation information indicates the location of that stimulation. In an example embodiment of the present invention, a computer system provides a graphical user interface in which amplitude settings for a directional electrode leadwire are plotted in curves at planes that are perpendicular to the central axis of the leadwire according to the described coordinate system including longitudinal, angular, and radii values.

Figure 2:
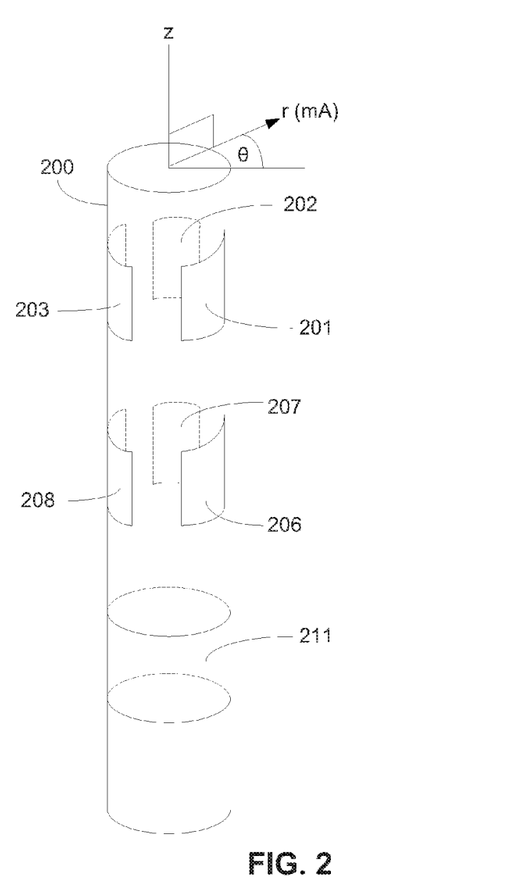
FIG. 2 shows an example leadwire model that is displayable by a system in a user interface, and further shows relative thereto a coordinate system for indicating amplitude information for directional electrodes, according to an example embodiment of the present invention.

FIG. 2 shows an example leadwire that includes a plurality of directional electrodes. In FIG. 2, the example leadwire 200 includes, at a first longitudinal level of the leadwire, three directional electrodes 201, 202, and 203, at a second longitudinal level of the leadwire, three directional electrodes 206, 207, and 208, and, at a third longitudinal level, a cylindrically symmetrical electrode 211 that is configured for generating a stimulation at approximately equal levels about the leadwire 200. While the directional electrodes are shown to be provided in groups about the leadwire, in an example embodiment, the leadwire 200 includes a circumferential directional electrode that continuously extends around the leadwire, but is controllable for generating stimulations at different levels in different directions from the leadwire.

FIG. 2 further shows a coordinate system in which amplitude values can be plotted using the 'z', 'θ', and 'r' coordinates. The coordinate system is shown relative to the illustrated leadwire 200, thereby showing the meaning of the coordinate values, which represent positional and amplitude information relative to the leadwire 200. Although the leadwire 211 is not a directional leadwire, the same coordinate system can be used for the cylindrically symmetrical leadwire too.

Figure 3:
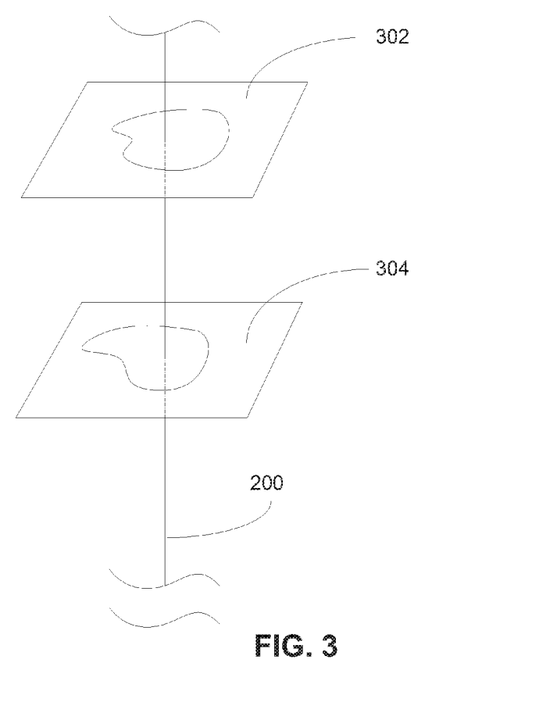
FIG. 3 shows amplitude information graphs for directional electrodes in a three-dimensional perspective, according to an example embodiment of the present invention.

FIG. 3 shows an example user interface display of graphed amplitude settings values using the described coordinate system for a directional leadwire. For example, a graph 302 and/or 304 is drawn with a perspective of being in a two dimensional plane perpendicular to the leadwire 200. Each of the illustrated graphs includes a shape formed by plotted values, for example, representing therapeutic threshold minimum values, i.e., values estimated as the minimum required amplitude for stimulation, where the estimated threshold minimum values vary depending on direction from the leadwire 200 at the longitudinal position of the leadwire 200 at which the plane is drawn. The graphs can alternatively represent maximum amplitude values above which a side effect is estimated to occur. As described below, graphs showing a combination of this information can also be provided.

Stimulation using a combination of electrodes at an one longitudinal level can produce stimulation values characterized by a stimulation at a direction which can be between the electrodes. Similarly, stimulation using a combination of electrodes at a plurality of longitudinal levels can produce stimulation values characterized by a stimulation at a level between electrodes above and below. Therefore, the displayed graphs need not be a longitudinal positions at which there are electrodes (although an alternative example embodiment can be provided in which the graphs are displayed only at longitudinal positions at which at least one electrode is located). In an example embodiment, using graphs plotting stimulations values characterized as occurring between electrodes by combinations of stimulations of those electrodes, the system plots a plurality of two dimensional graphs of stimulation values in a plurality of continuous layers to form a three dimensional graph volume.

In an example embodiment of the present invention, the system displays a model of the leadwire 200, e.g., as shown in FIG. 2 and further displays one or more graphs as shown in FIG. 3. The graphs can be displayed in a separate display area as that in which the model of the leadwire 200 is displayed, or can be displayed overlaid on the model of the leadwire 200. In an example embodiment of the present invention, the system and method of the present invention provides a graphical user interface including view rotation controls, by which a user can rotate the displayed model of the leadwire 200 and the displayed graphs.

Figure 4A:
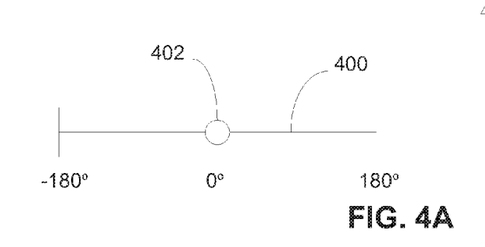
FIG. 4A shows a slider control for rotating a leadwire model, according to an example embodiment of the present invention.

For example, FIG. 4A shows a slide bar 400, with the center set at 0°, the right end at +180°, and the left end at −180°. A particular longitudinal line at a predetermined point along the circumference of the leadwire is selected as corresponding to 0°. The user can shift a slider control 402 along the slide bar 400, in response to which the system correspondingly rotates the model of the leadwire 200 (and the associated graphs). For example, in an example embodiment, the system shifts the model of the leadwire 200 so that that the selected angular portion of the leadwire 200 is positioned parallel with the surface of the screen in which the user interface is displayed.

Figure 4B:
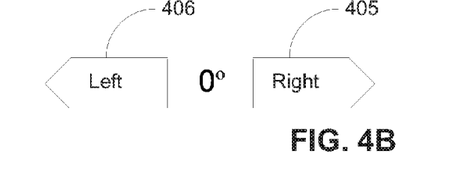
FIG. 4B shows left and right buttons for rotating a leadwire model, according to an example embodiment of the present invention.

Alternatively (or additionally), as shown in FIG. 4B, a right button 405 and a left button 406 can be displayed, which buttons are selectable using an input device, e.g., via point and click, touch, or any other suitably appropriate selection device/method, in response to which selection the model of the leadwire 200 is rotated towards the right or towards the left by a predetermined number of degrees per selection. In an example embodiment, the system displays an indication of the number of degrees the model of the leadwire 200 has been rotated, for example, as shown in FIG. 4B, between the selectable right and left buttons 405/406.

Figure 4C:
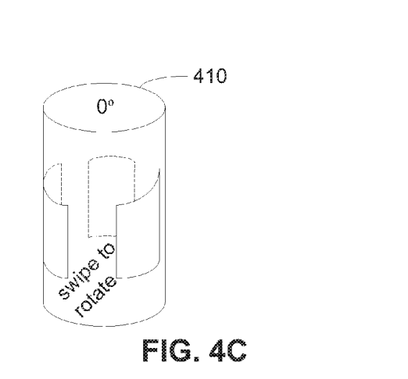
FIG. 4C shows a draggable interface component for rotating a leadwire model, according to an example embodiment of the present invention.

Alternatively (or additionally), as shown in FIG. 4C, the model of the leadwire 200 or a separate leadwire rotation control 410 that is selectable by the user and draggable to the right or to the left is displayed, where, in response to the dragging of the leadwire model 200 or the separate rotation control 410, the system correspondingly rotates the model of the leadwire 200 and the graphs. In an example embodiment, as shown in FIG. 4C, the system displays an indication of the number of degrees the model of the leadwire 200 has been rotated, for example, as shown in FIG. 4C, in a top cross-section of the leadwire representation of the leadwire rotation control 410.

Figure 4D:
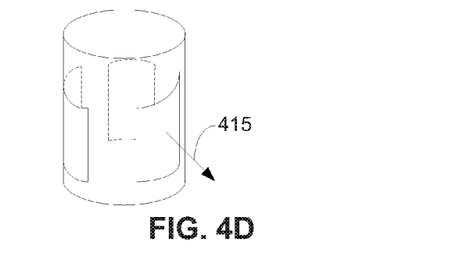
FIG. 4D shows a user interface control including a ray that is user-draggable rotationally about a point of origin corresponding to a leadwire and inward and outward with respect to the point of origin, for user modification of electrical parameters, according to an example embodiment of the present invention.

In an example embodiment of the present invention, representations of respective electrodes in the model of the leadwire 200 or in the leadwire rotation control 410 are selectable, in response to which input, the system is configured to obtain user input of one or more settings to be set for the selected electrode. In an example embodiment, the system is configured to display one or more data fields in which to input parameter values for the selected electrode. In an example embodiment, as shown in FIG. 4D, the system is configured to display a ray 415 extending from the selected electrode, which ray 415 the user can select and drag in a direction away from the representation of the leadwire 200 or towards the representation of the leadwire 200, where the system interprets dragging in the direction away from the representation of the leadwire 200 as an input to increase the amplitude setting, and the system interprets dragging back toward the representation of the leadwire 200 as an input to decrease the amplitude. The input can be by a clinician and, in an example embodiment, the system is configured to receive an instruction in response to which the system is configured to apply the modified setting to an implanted pulse generator that causes the leadwire 200 to produce the stimulation. Alternatively or additionally, the user-modification of the settings is for input of stimulation programs for which the system outputs information, e.g., a VOA, and/or other information, based on which the user can select a program to apply to the implanted pulse generator.

In an example embodiment of the present invention, the user interface display including the model of the leadwire 200 further includes a ray, like described ray 415, that extends from the model of the leadwire 200, and the ray is selectable and draggable towards the right and towards the left to modify a directionality of a stimulation, and inwards and outwards with respect to the model of the leadwire 200 to modify an amplitude of the stimulation in the selected direction.

Figure 5:
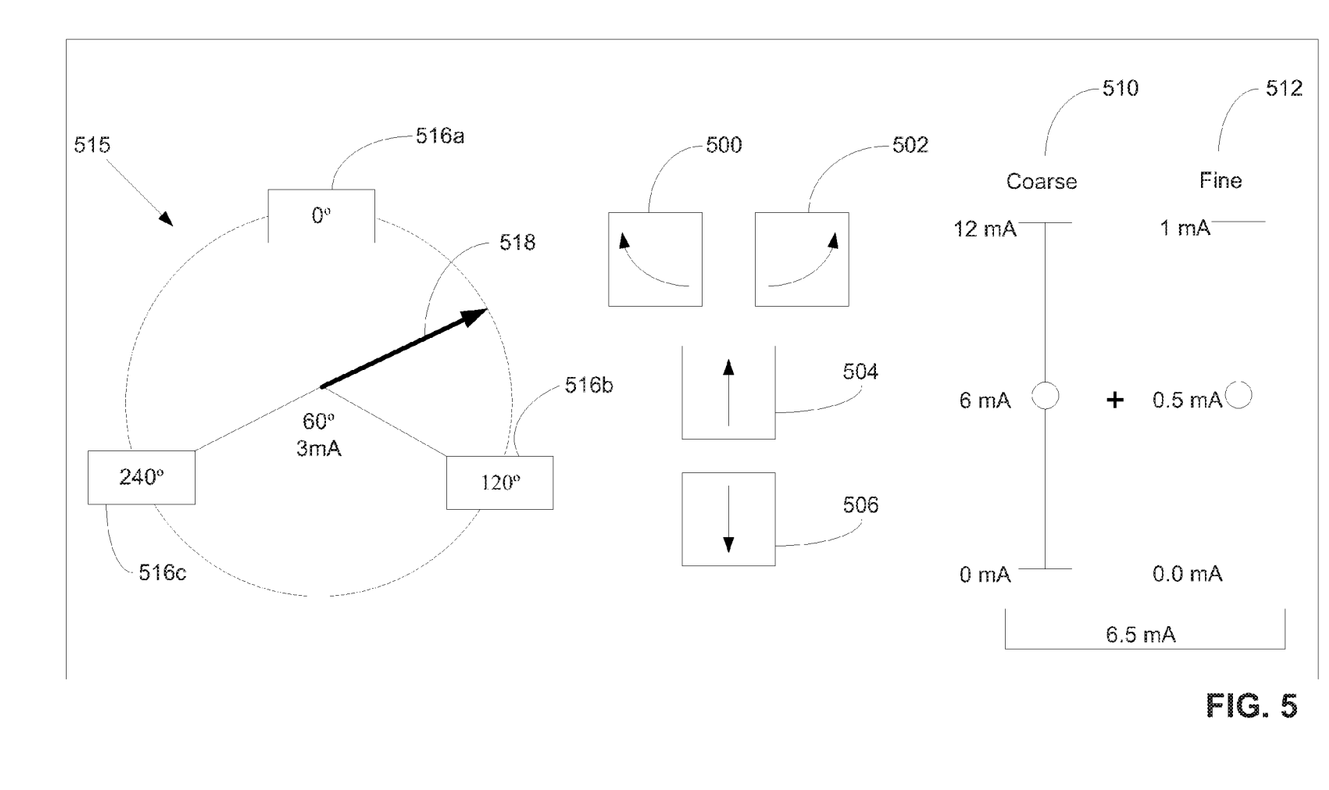
FIG. 5 illustrates user interface components, by user interaction with which a system is configured to receive input of stimulation parameters, according to an example embodiment of the present invention.

FIG. 5 shows a part of a graphical user interface, according to an example embodiment, that can be displayed in a display device and that includes controls selectable by a user for input of stimulation settings, including a directionality, amplitude, and longitudinal locations relative to the leadwire, for a stimulation. The user interface includes a rotate left button 500, for modifying by the system of the directionality of a stimulation by clockwise rotation about the leadwire by a predetermined incremental amount, responsive to each selection thereof. The user interface further includes a rotate right button 502, for modifying by the system of the directionality of the stimulation by counter-clockwise rotation about the leadwire by a predetermined incremental amount, responsive to each selection thereof. The user interface further includes one or more slider bars by which to modify the amplitude of the stimulation. For example, as shown in FIG. 5, in an example embodiment the user interface includes a coarse slider bar 510 in response to sliding of the slider control of which, the system modifies the amplitude by a first predetermined amount, e.g., a single digit whole number, for each change in position of the slider control; and also includes a fine slider bar 512 in response to sliding of the slider control of which, the system modifies the amplitude by a second predetermined amount smaller than the first predetermined amount, for fine increments between the selected coarse value set by the position of the coarse slider bar 510 and the next higher coarse value corresponding to the position of the coarse slider bar 510 that follows the current position thereof. For example, the coarse slider bar 510 can be set to be shifted between positions 0 and 12, a single whole number at a time, and the fine slider bar 512 can be set to be shifted between positions 0.0 and 0.9, a tenth at a time, so that for whichever value is set by the coarse slider bar 510, the value is further settable to an additional fractional amount.

The user interface further includes an up button 504 and a down button 506, for selection by the user of the longitudinal location along the leadwire at which the stimulation is to occur.

In an example embodiment, as shown in FIG. 5, the user interface further includes a, e.g., two dimensional, settings map 515 that shows present values of the settings with respect to directionality and amplitude of the stimulation. The settings map 515 includes a respective representations 516a-516c of each electrode at a particular longitudinal level. The settings map 515 includes a bar 518 angularly positioned according to the directionality of the stimulations according to the present settings, and whose length corresponds to the presently set amplitude of the stimulation. As the user provides input, e.g., via controls 500, 502, 510, and 512, to modify the directionality and/or amplitude, the bar 518 is rotated and/or shortened or lengthened. In an example embodiment, as shown in FIG. 5, the present angle and amplitude are displayed in the settings map 515.

In an example embodiment of the present invention, the user interface shown in FIG. 5, described above, instead of providing for longitudinally steering the electrical, e.g., current, using the up and down buttons 504 and 506, the system provides for receiving respective input for each longitudinal level of electrodes, each respective input indicating a respective direction and amplitude, e.g., by use of the controls 500, 502, 510, and/or 512, and/or other input controls, e.g., as described herein. For example, for the leadwire 200 as shown in FIG. 2, which includes electrodes 201-203 at a first level, electrodes 206-208 at a second level, and electrode 211 at a third level, the system outputs three user interface sections, e.g., like that shown in FIG. 5, for separately inputting the directional and amplitude settings of the stimulation.

According to a variant of this embodiment, the buttons 504 and 506 are omitted since current steering is not supported. Alternatively, buttons 504 and 506 are provided, but, according to this embodiment, their selections do not cause the above-described current steering, but rather are used for traversing between settings of different electrode levels of the leadwire. For example, the user can use the controls shown in FIG. 5 (or other controls) to set the direction and amplitude for electrodes at a first longitudinal level of the leadwire, and then select one of buttons 504 and 506 to set the settings for the electrodes of, respectively, the next higher or lower longitudinal level of the leadwire.

In an example embodiment of the present invention, the stimulation controls and the settings map 515 are displayed in an interface in which a three-dimensional perspective of a model of the leadwire 200, e.g., as shown in FIG. 2, is also displayed, which model is rotatable, for example, as discussed above with respect to any of FIGS. 4A-4C, and the rotational orientation of the settings map 515 is set by the system to correspond to the rotational orientation of the three-dimensional perspective of the model of the leadwire 200, such that the settings map 515 is rotated when the three-dimensional perspective of the model is rotated.

Figure 6:
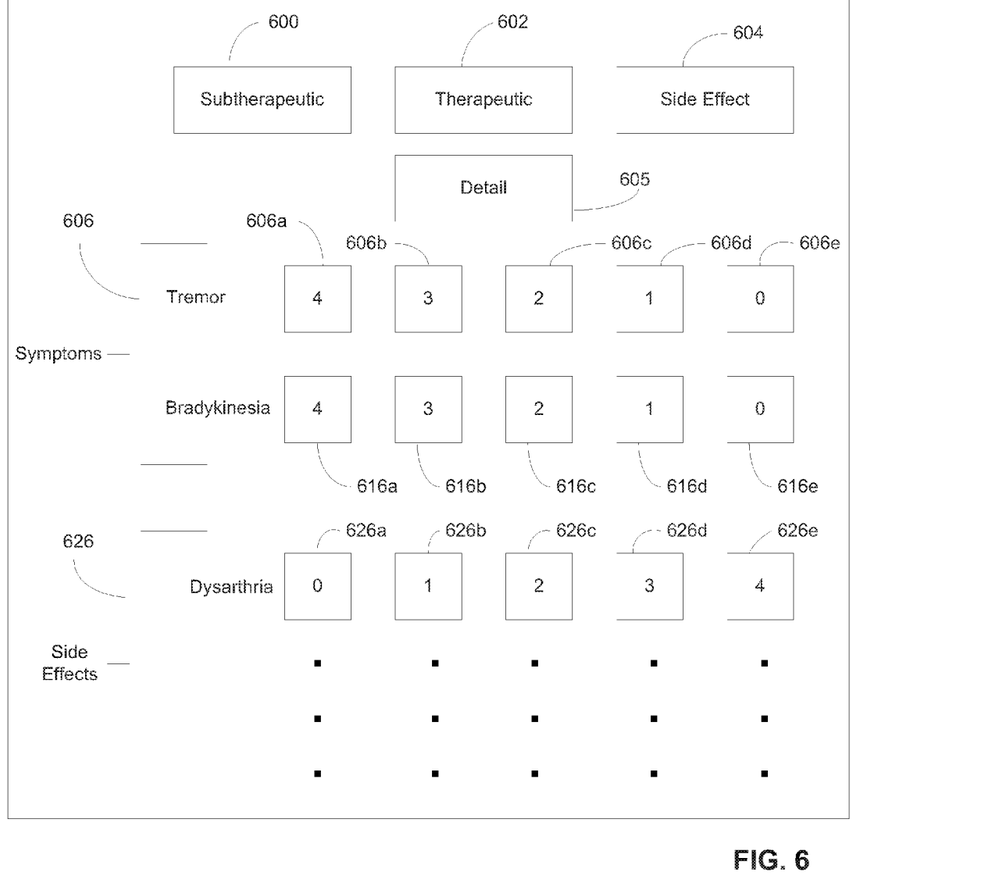
FIG. 6 illustrates user interface components, by user interaction with which a system is configured to receive input of annotations regarding stimulation settings, according to an example embodiment of the present invention.

As described above with respect to FIG. 3, according to example embodiments of the present invention, the system displays one or more graphs providing certain threshold (e.g., minimums and/or maximums) information using longitudinal, angular, and radii coordinates, regarding stimulation at various directions about the leadwire. In an example embodiment of the present invention, the system includes an interactive user interface with which a user can interact to input information usable by a processor to generate graphs such as those described with respect to FIG. 3. For example, FIG. 6 shows an example annotation control interface including annotation controls selectable by a user for inputting information concerning presently indicated settings. For example, in an example embodiment, the annotation control interface includes a sub-therapeutic button 600, which, if selected by the user, causes a processor of the system to record in memory information indicating that a stimulation at the presently indicated settings fail to produce a sufficiently therapeutic effect. In an example embodiment, the annotation control interface additionally or alternatively includes a therapeutic button 602, which, if selected by the user, causes a processor of the system to record in memory information indicating that a stimulation at the presently indicated settings fail produce a sufficiently therapeutic effect. In an example embodiment, the annotation control interface additionally or alternatively includes an over limit button 604, which, if selected by the user, causes a processor of the system to record in memory information indicating that a stimulation at the presently indicated settings produces an adverse side effect.

A therapy can cause both a therapeutic effect and an adverse side effect. Therefore, according to an example embodiment of the present invention, the system allows for input indicating both the therapeutic effect and the side effect.

According to an alternative example embodiment of the present invention, the annotation control interface includes a list of symptoms with an associated one or more input fields or selectable controls (e.g., discrete or by slider bar) by which to indicate a degree of therapeutic effect for that respective symptom and/or a list of adverse side effects with an associated one or more input fields or selectable controls (e.g., discrete or by slider bar) by which to indicate a degree to which the respective side effect is caused by the stimulation at the presently indicated settings. For example, as shown in FIG. 6, a symptoms section 606 lists the example symptoms of "tremor" and "bradykinesia" alongside each of which is a respective series of buttons selectable for inputting a respective degree of therapeutic effect for the respective symptom. For example, FIG. 6 shows a set of 5 buttons 606a-606e for inputting respective degrees of therapeutic effect for the symptom of tremor, for example, where selection of button 606a indicates a highest therapeutic effect and selection of button 606e indicates a lowest therapeutic effect (buttons 606b-606d indicating intermediate and progressively decreasing therapeutic effect). FIG. 6 similarly shows a set of 5 buttons 616a-616e similarly operable for the symptom of bradykinesia. FIG. 6 similarly shows a side effect section 626 which lists the example adverse side effect of "dysarthia" alongside which is a respective set of 5 buttons 626a-626e for inputting respective degrees of the adverse side effect of dysarthia, for example, where selection of button 626a indicates a lowest amount of side effect and selection of button 626e indicates a highest amount of side effect (buttons 626b-626d indicating intermediate and progressively increasing side effect).

In an example embodiment of the present invention, the controls for inputting specific therapeutic and side effect information, including identification of particular symptoms for which therapeutic effect is provided and/or identification of particular adverse side effects produced by the therapy, such as controls of sections 606 and 626, and the controls for inputting the more generalized information as to whether a therapeutic effect has been provided and/or a side effect has been produced, such as controls 600-604 are all provided by the system. For example, in an example embodiment of the present invention, the system initially displays controls 600-604, and, responsive to selection of a "details" button or tab 605, the system displays the controls for inputting the information in detailed form. For example, the system updates the interface to simultaneously display all of the controls 600-604 and 606a-626e. Alternatively, the system responsively replaces the generalized controls with the more specific controls. According to either embodiment, the system, in an example embodiment, toggles between the two types of displays responsive to repeated selection of the details button 605.

According to an example embodiment of the present invention, the system is configured to output different graphs as described with respect to FIG. 3 depending on user selectable filter criteria. For example, the user can filter for therapeutic effect related to tremor, in response to which filter the system is configured to output graphs like those shown in FIG. 3 indicating direction-dependent minimum amplitude values for producing a therapeutic effect for tremor, or can similarly filter for therapeutic effect related to bradykinesia. In an example embodiment, without input of a filter criterion, the system outputs a graph based on, for example, minimum amplitude values for producing a therapeutic effect of any kind, i.e., not limited to any one type of selected therapeutic effect.

Similarly, in an example embodiment of the present invention, the user can filter by adverse side effect, e.g., by dysarthia, in response to which filter the system is configured to output graphs like those shown in FIG. 3 indicating direction-dependent maximum amplitude values above which the particular selected side effect is expected to occur. In an example embodiment, without input of a filter criterion, the system outputs a graph based on, for example, maximum amplitude values beyond which any side effect has been recorded to have occurred, i.e., not limited to any one type of selected side effect.

Similarly, instead of or in addition to filtering by type of therapeutic effect and/or side effect, the system provides for filtering based on degree. For example, referring to FIG. 6, the user can filter for only those therapeutic effects indicated by at least a strength of that represented by button 606c, etc. Another example filter criterion is time. For example, the user can filter for graph generation based on input provided in a user-selected time period.

According to an example embodiment, if information is entered indicating the occurrence of a therapeutic effect or side effect, without additional details, e.g., by operation of one or more of the buttons 600-604, without providing additional details concerning degree or type, the system uses such information for the generation of a graph unconstrained by the above-described input criterion of degree and/or type, but does not consider such information for graphs provided in response to a user request constrained by such input criteria.

In an example embodiment of the present invention, the system is configured to output a combination of discrete graphs corresponding to respective types and/or degree. For example, in a plane drawn at a particular longitudinal position of the leadwire, the system outputs one or more graphs corresponding to therapeutic effect for tremor (at one or more degrees of effect) and one or more graphs corresponding to therapeutic effect for bradykinesia (at one or more degrees of effect). The system outputs indicia that identify the effect (and/or degree thereof) to which the different graphs correspond. For example, different colors (and/or hue, saturation, and/or transparency) can be used to represent different effects, and/or different labels can be displayed, e.g., perpetually or when selected or when a pointer is moved over or in close proximity to the graph. The system can similarly generate a plane of overlapping graphs corresponding to different side effects (and/or side effect seventies).

Figure 7:
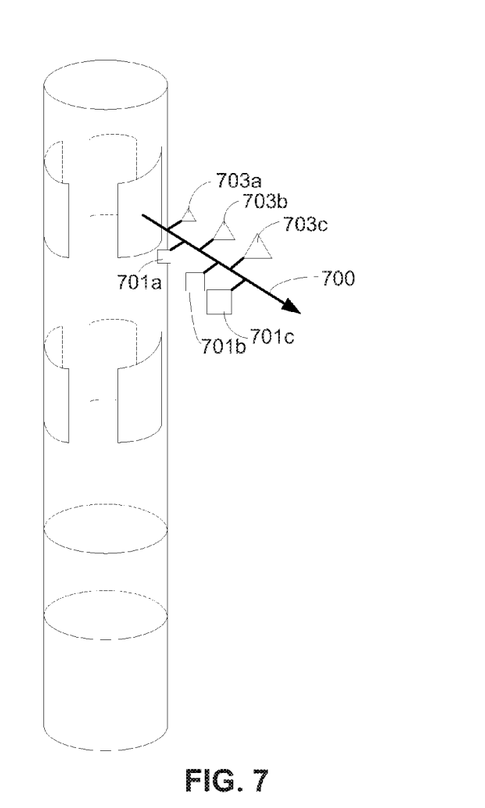
FIG. 7 illustrates user interface components for outputting variations in effect for variations in amplitude in a particular direction, according to an example embodiment of the present invention.

In an example embodiment of the present invention, instead of or in addition to a user interface display in which a plurality of graphs for different therapeutic effects, and/or side effects, and/or degrees thereof are included in a single plane, the graphs indicating directional dependency of the amplitude about the leadwire, the system is configured to indicate a variation of stimulation effect (e.g., adverse side effect or therapeutic effect) along a single selected direction from the leadwire as amplitude is increased. For example, FIG. 7 shows a user interface display including a model of a leadwire 200 with a ray 700 including markings at different locations of the ray corresponding to respective distances from the leadwire, which further corresponds to respective amplitude values. The markings can be provided at equal intervals. Alternatively, the markings can be provided wherever there is an appreciable change to the effect (e.g., where the system is programmed to indicate where a predefined difference value or percentage is reached). In an example embodiment, the markings indicate the degree of effect. For example a textual label or other indicia can be used. Further, in an example embodiment, a single ray is marked with different types of indicia for different types of information, e.g., different side effects or therapeutic effects. For example, ray 700 is marked by squares 701a-701c and triangles 703a-703c of different sizes, where squares 701a-701c indicate one type of effect, e.g., therapeutic effect for tremor, and triangles 703a-703c indicate another type of effect, e.g., therapeutic effect for bradykinesia, and where the sizes indicate the degree of such effect, e.g., small shapes indicating a slight effect and large shapes indicating a large effect.

While FIG. 7 shows a single ray 700 in a single direction, in an example embodiment, the system displays a plurality of such rays, each in a respective direction. For example, in an example embodiment, the system generates a display with a plurality of evenly spaced rays cylindrically about the leadwire. In an alternative example embodiment, the system is configured for receiving user input of one or more angles (i.e., directions), and the system accordingly displays respective rays for each of the input angles. In an example embodiment, the system, by default outputs a single ray for each directional electrode.

Figure 8:
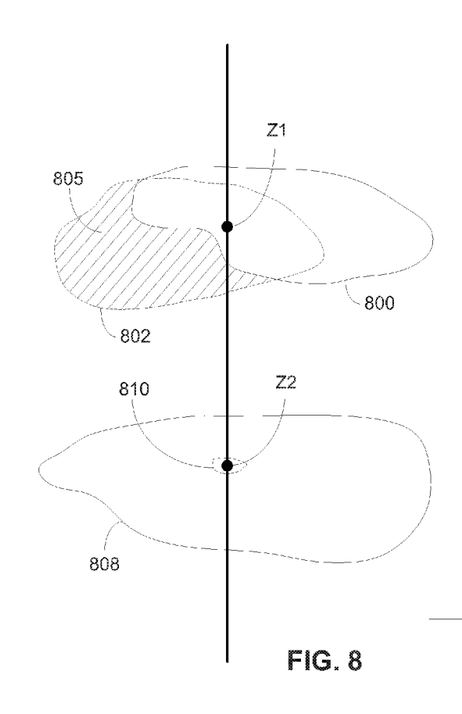
FIG. 8 illustrates a user interface display of information concerning suitable stimulation amplitude parameters for directional electrodes using graphs in a three-dimensional perspective, according to an example embodiment of the present invention.

As shown in FIG. 8, in an example embodiment of the present invention, the system is configured to output, in a single plane, graphs for both therapeutic effect and adverse side effect, which graphs can overlap depending on the respective minimum and maximum amplitude values of the graphs in the different directions about the leadwire. A user can thereby determine a range of amplitudes and an angular range about the leadwire at which to set the stimulation. In an example embodiment, the system is configured to mark a graph region determined to be suitable for stimulation based on the relationship between the area of the two graphs (where the graphs do indicate the existence of such a region).

For example, FIG. 8 shows a therapy onset graph 800 and a side effects graph 802 within a plane at longitudinal position z1. In an example embodiment, the system outputs indicia indicating which graph represents therapy onset values and which graph represents adverse side effects, each by line type or color and/or textual indicia, etc. It further includes a cross-hatched region 805, the cross-hatching indicating that region to represent suitable stimulation parameters. Any other suitably appropriate region indicia can be used, e.g., highlighting, coloring, or textual indicia, etc. The cross-hatched region is determined to represent suitable parameters because the parameters corresponding to that region are indicated to produce a therapeutic effect without producing an adverse side effect.

FIG. 8 further shows a therapy onset graph 808 and a side effects graph 810 within a plane at longitudinal position z2. No cross-hatched region is included because there is no suitable range of stimulation parameters at longitudinal position z2, since, in all directions about the leadwire, intolerable side effects set in at lower amplitudes than those at which therapeutic effects are first attained.

It is noted that that there may be certain adverse side effects that are tolerable and there may be certain therapeutic effects that are insignificant. The system is programmed to produce the graphical information for certain predetermined side effects and/or therapeutic effects. Additionally, in an example embodiment, the system includes a user interface via which a user can select one or more side effects and/or one or more therapeutic effects on which basis to generate the graphs.

Figure 9A:
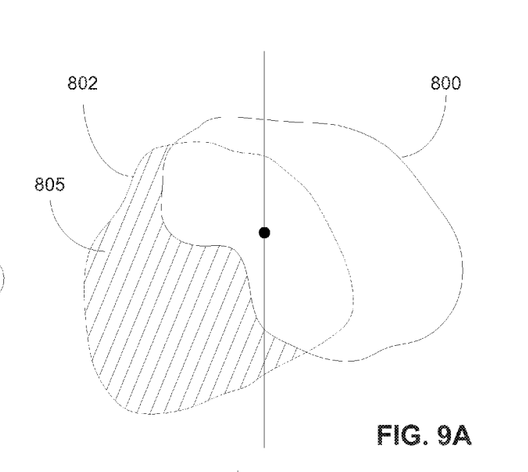
FIGS. 9A and 9B show user interface displays of the graphs of FIG. 8 in a two-dimensional perspective, according to an example embodiment of the present invention.
Figure 9B:
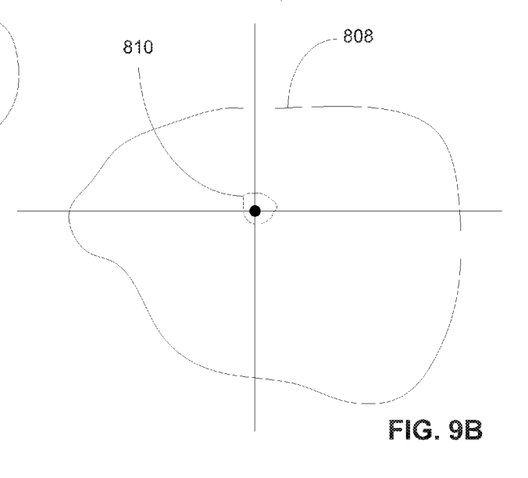

When the graphs are provided in a three-dimensional perspective about the model of the leadwire 200, the leadwire model can partially obscure portions of the graphs. Although, as discussed above, example embodiments provide a control for rotating the model, so that the graphs can be rotated and viewed at the different angles, a user may desire to view entire graphs at a time for the respective longitudinal positions at which they are generated. Additionally, when the graphs are provided in a three-dimensional perspective, precise dimensions of the graph shape are distorted to account for depth in a two-dimensional display screen, for example, as can be seen by a comparison of the graphs in FIG. 8 and their two-dimensional perspective counterparts shown in FIGS. 9A and 9B. Accordingly, in an example embodiment of the present invention, the system displays the graphs in a two dimensional view, in which the graphs of a single longitudinal position are displayed such that planes formed by the graphs are parallel to the surface of the display area, e.g., parallel to the surface of a display screen. For example, FIG. 9A shows the graphs 800 and 802 in a two-dimensional view with the leadwire virtually extending perpendicularly to the display screen, and FIG. 9B shows the graphs 808 and 810 in a two-dimensional view with the leadwire virtually extending perpendicularly to the display screen. In an example embodiment of the present invention, a two-dimensional view of graphs is displayed for only a single one of the longitudinal positions of the leadwire at any one time. Alternatively, in an example embodiment, different two-dimensional graph views for a plurality of longitudinal positions are simultaneously displayed in different respective display areas of the display screen, e.g., each area including respective indicia indicating the respective longitudinal position to which it corresponds.

In an example embodiment of the present invention, the system includes a control selectable for toggling between a three dimensional view of the graphs and two dimensional views of the graphs.

In an example embodiment of the present invention, for a set of stimulation parameters, the system outputs a graphical representation of the parameters in the form of a ray extending from a model of the leadwire, where the directionality and length of the ray represents a directionality of the stimulation produced by the parameters and the electrical amplitude. In an example embodiment, the system further outputs information regarding tissue stimulation produced by the electrical stimulation parameters represented by the array. For example, in an example embodiment, the system displays a first user interface fame identifying one or more of the stimulation parameters and/or including a graphical representation thereof, e.g., in the form of the described array, and further displays a second user interface section displaying an estimated VOA, e.g., as described in the '330, '312, '340, '343, and '314 applications, corresponding to the indicated and/or represented stimulation parameters.

An example embodiment of the present invention is directed to one or more processors, which can be implemented using any conventional processing circuit and device or combination thereof, e.g., a Central Processing Unit (CPU) of a Personal Computer (PC) or other workstation processor, to execute code provided, e.g., on a hardware computer-readable medium including any conventional memory device, to perform any of the methods described herein, alone or in combination, and to generate any of the user interface displays described herein, alone or in combination. The one or more processors can be embodied in a server or user terminal or combination thereof. The user terminal can be embodied, for example, as a desktop, laptop, hand-held device, Personal Digital Assistant (PDA), television set-top Internet appliance, mobile telephone, smart phone, etc., or as a combination of one or more thereof. Specifically, the terminal can be embodied as a clinician programmer terminal, e.g., as referred to in the '330, '312, '340, '343, and '314 applications. Additionally, as noted above, some of the described methods can be performed by a processor on one device or terminal and using a first memory, while other methods can be performed by a processor on another device and using, for example, a different memory.

The memory device can include any conventional permanent and/or temporary memory circuits or combination thereof, a non-exhaustive list of which includes Random Access Memory (RAM), Read Only Memory (ROM), Compact Disks (CD), Digital Versatile Disk (DVD), and magnetic tape.

An example embodiment of the present invention is directed to one or more hardware computer-readable media, e.g., as described above, having stored thereon instructions executable by a processor to perform the methods and/or provide the user interface features described herein.

An example embodiment of the present invention is directed to a method, e.g., of a hardware component or machine, of transmitting instructions executable by a processor to perform the methods and/or provide the user interface features described herein.

The above description is intended to be illustrative, and not restrictive. Those skilled in the art can appreciate from the foregoing description that the present invention can be implemented in a variety of forms, and that the various embodiments can be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and the following listed features.

What is claimed is:

1. A computer-implemented method, comprising:
   for each of a plurality of directions around a single longitudinal position along a leadwire:
      plotting, by a computer processor, a respective point at a distance from the leadwire that corresponds to a minimum electrical amplitude in that direction required to produce a therapeutic stimulation effect, thereby forming a first set of plotted points; and
      plotting, by the processor, a respective point at a distance from the leadwire that corresponds to a maximum electrical amplitude in that direction above which an adverse stimulation side effect is expected to occur, thereby forming a second set of plotted points;
      wherein one of: (a) the first and second sets of plotted points are plotted in a two-dimensional graph by which the plotted points form a plane that is perpendicular to the leadwire, and (b) the first and second sets of plotted points are plotted in a three-dimensional graph relative to the leadwire;
   for a set of stimulation parameters including an electrical amplitude, outputting, by the processor, on the two-dimensional graph or three-dimensional graph a graphical representation of the stimulation parameters in a form of a ray, where a directionality and length of the ray represents a directionality of stimulation produced by the stimulation parameters and the electrical amplitude, respectively; and
   in response to user manipulation of the ray, determining, by the processor, a modified set of stimulation parameters corresponding to the user manipulation of the ray and outputting the modified set of stimulation parameters for delivery to an implanted pulse generator to produce stimulation using the modified set of stimulation parameters.

2. The method of claim 1, further comprising:
   highlighting a region formed by points corresponding to amplitudes that are above respective plotted minimum amplitudes and below respective plotted maximum amplitudes, wherein a particular point corresponds to an amplitude that is above a respective plotted minimum amplitude and below a respective plotted maximum amplitude when the particular point is at a direction from the leadwire for which the minimum plotted amplitude is nearer the leadwire than the particular point and for which the maximum plotted amplitude is farther from the leadwire than the particular point.

3. The method of claim 1, further comprising:
   for each of a plurality of stimulation parameter sets, receiving user input indicating a respective clinical effect which is either the therapeutic stimulation effect or the adverse stimulation side effect.

4. The method of claim 3, further comprising:
   displaying in a user interface a first button user-selectable for indicating that a stimulation parameter set produced a therapeutic stimulation effect, a second button user-selectable for indicating that the stimulation parameter set failed to produce a therapeutic stimulation effect, and a third button user-selectable for indicating that the stimulation parameter set produced an adverse stimulation side effect.

5. The method of claim 1, further comprising displaying, by the processor and relative to either the two-dimensional graph or the three-dimensional graph, a model of the leadwire having a plurality of directional electrodes disposed at different longitudinal levels along the model of the leadwire.

6. The method of claim 5, wherein the ray is displayed as originating from one of the directional electrodes of the leadwire.

7. The method of claim 1, wherein the user manipulation of the ray is a rotation of the ray.

8. The method of claim 1, wherein the user manipulation of the ray is a change in a length of the ray.

9. The method of claim 1, further comprising indicating a region that is outside the first set of plotted points and inside the second set of plotted points as a region representing suitable stimulation parameters.

10. The method of claim 1, further comprising repeating the plotting steps for a second longitudinal position.

11. A non-transitory computer-readable medium having stored thereon instructions executable by a processor, wherein the instructions comprise:
   for each of a plurality of directions around a single longitudinal position along a leadwire:
      plot a respective point at a distance from the leadwire that corresponds to a minimum electrical amplitude in that direction required to produce a therapeutic stimulation effect, thereby forming a first set of plotted points; and
      plot a respective point at a distance from the leadwire that corresponds to a maximum electrical amplitude in that direction above which an adverse stimulation side effect is expected to occur, thereby forming a second set of plotted points;

wherein one of: (a) the first and second sets of plotted points are plotted in a two-dimensional graph by which the plotted points form a plane that is perpendicular to the leadwire, and (b) the first and second sets of plotted points are plotted in a three-dimensional graph to the leadwire;

for a set of stimulation parameters including an electrical amplitude, output on the two-dimensional graph or three-dimensional graph a graphical representation of the stimulation parameters in a form of a ray, where a directionality and length of the ray represents a directionality of stimulation produced by the stimulation parameters and the electrical amplitude, respectively; and in response to user manipulation of the ray, determine a modified set of stimulation parameters corresponding to the user manipulation of the ray and outputting the modified set of stimulation parameters for delivery to an implanted pulse generator to produce stimulation using the modified set of stimulation parameters.

12. The non-transitory computer-readable medium of claim 11, wherein the instructions further comprise display in a user interface a first button user-selectable for indicating that a stimulation parameter set produced a therapeutic stimulation effect, a second button user-selectable for indicating that the stimulation parameter set failed to produce a therapeutic stimulation effect, and a third button user-selectable for indicating that the stimulation parameter set produced an adverse stimulation side effect.

13. The non-transitory computer-readable medium of claim 11, wherein the instructions further comprise display, relative to either the two-dimensional graph or the three-dimensional graph, a model of the leadwire having a plurality of directional electrodes disposed at different longitudinal levels along the model of the leadwire.

14. The non-transitory computer-readable medium of claim 11, wherein the instructions further comprise indicate a region that is outside the first set of plotted points and inside the second set of plotted points as a region representing suitable stimulation parameters.

15. The non-transitory computer-readable medium of claim 11, wherein the instructions further comprise repeat the plotting instructions for a second longitudinal position.

16. A system, comprising:
a display; and
a processor coupleable to the display and configured and arranged to perform the following actions:
for each of a plurality of directions around a single longitudinal position along a leadwire:
plot, on the display, a respective point at a distance from the leadwire that corresponds to a minimum electrical amplitude in that direction required to produce a therapeutic stimulation effect, thereby forming a first set of plotted points; and
plot, on the display, a respective point at a distance from the leadwire that corresponds to a maximum electrical amplitude in that direction above which an adverse stimulation side effect is expected to occur, thereby forming a second set of plotted points;

wherein one of: (a) the first and second sets of plotted points are plotted in a two-dimensional graph by which the plotted points form a plane that is perpendicular to the leadwire, and (b) the first and second sets of plotted points are plotted in a three-dimensional graph to the leadwire;

for a set of stimulation parameters including an electrical amplitude, output on the display and on the two-dimensional graph or three-dimensional graph a graphical representation of the stimulation parameters in a form of a ray, where a directionality and length of the ray represents a directionality of stimulation produced by the stimulation parameters and the electrical amplitude, respectively; and in response to user manipulation of the ray, determine a modified set of stimulation parameters corresponding to the user manipulation of the ray and outputting the modified set of stimulation parameters for delivery to an implanted pulse generator to produce stimulation using the modified set of stimulation parameters.

17. The system of claim 16, wherein the actions further comprise display in a user interface on the display a first button user-selectable for indicating that a stimulation parameter set produced a therapeutic stimulation effect, a second button user-selectable for indicating that the stimulation parameter set failed to produce a therapeutic stimulation effect, and a third button user-selectable for indicating that the stimulation parameter set produced an adverse stimulation side effect.

18. The system of claim 16, wherein the actions further comprise display on the display and relative to either the two-dimensional graph or the three-dimensional graph, a model of the leadwire having a plurality of directional electrodes disposed at different longitudinal levels along the model of the leadwire.

19. The system of claim 16, wherein the actions further comprise indicate on the display a region that is outside the first set of plotted points and inside the second set of plotted points as a region representing suitable stimulation parameters.

20. The system of claim 16, wherein the actions further comprise repeat the plotting actions for a second longitudinal position.

* * * * *